(12) United States Patent
Gum et al.

(10) Patent No.: US 9,489,734 B2
(45) Date of Patent: Nov. 8, 2016

(54) DETERMINATION OF A BODY PART POSITION DURING RADIATION THERAPY

(75) Inventors: Franz Gum, Munich (DE); Stephan Erbel, Munich (DE)

(73) Assignee: Brainlab AG, Feldkirchen (DE)

( * ) Notice: Subject to any disclaimer, the term of this patent is extended or adjusted under 35 U.S.C. 154(b) by 206 days.

(21) Appl. No.: 13/977,252

(22) PCT Filed: Jan. 12, 2011

(86) PCT No.: PCT/EP2011/050351
§ 371 (c)(1),
(2), (4) Date: Jun. 28, 2013

(87) PCT Pub. No.: WO2012/095172
PCT Pub. Date: Jul. 19, 2012

(65) Prior Publication Data
US 2013/0287167 A1    Oct. 31, 2013

(51) Int. Cl.
A61N 5/10    (2006.01)
G06T 7/00    (2006.01)
A61B 6/00    (2006.01)

(52) U.S. Cl.
CPC ............. *G06T 7/0016* (2013.01); *A61B 6/547* (2013.01); *A61N 5/1049* (2013.01);
(Continued)

(58) Field of Classification Search
CPC .. A61B 6/0492; A61B 6/488; A61N 5/1048; A61N 5/1049; A61N 5/1064; A61N 5/1065; A61N 5/1067; A61N 5/1069; A61N 5/107; A61N 2005/1049; A61N 2005/1051; A61N 2005/1061; A61N 2005/1062
See application file for complete search history.

(56) References Cited

U.S. PATENT DOCUMENTS

2006/0074292 A1* 4/2006 Thomson et al. ............ 600/411
2007/0291895 A1   12/2007 Yin et al.

(Continued)

FOREIGN PATENT DOCUMENTS

EP    1 832 313    9/2007
WO    2006/039009    4/2006
(Continued)

OTHER PUBLICATIONS

International Search Report for International Application No. PCT/EP2011/050351 dated Jan. 12, 2011.
(Continued)

*Primary Examiner* — Thomas R Artman
(74) *Attorney, Agent, or Firm* — Tucker Ellis LLP (57) ABSTRACT

The present invention relates to a data processing method for use in the field of radiation therapy and for determining a position of a treatment body part relative to an actual arrangement of at least one position of a treatment beam issued by a treatment device, the position being called monitoring tissue position and the treatment body part being a soft tissue part of an anatomical structure of a patient; the data processing method being constituted to be performed by a computer and comprising the following steps: ● providing CBCT data describing a three-dimensional CBCT image of the anatomical structure, the three dimensional CBCT image representing the treatment body part and a bony structure in a relative position to each other, called tissue-bone pre-alignment position, at a point in time, called pre-alignment time; ● providing x-ray data describing information on a position of the bony structure, called monitoring bone position, relative to the actual arrangement at a point in, time during treatment, called monitoring time, the monitoring time being after the pre-alignment time; ● determining the monitoring tissue position of the treatment body part relative to the actual arrangement ○ based on the tissue-bone pre-alignment position represented by the CBCT image data, ○ based on the information on the monitoring bone position described by the x-ray data, and ○ based on a predefined relationship between a first relative position between the treatment body part and the bony structure at the pre-alignment time and a second relative position between the treatment body part and the bony structure at the monitoring time.

16 Claims, 3 Drawing Sheets

(52) U.S. Cl.
CPC .......... *A61N 5/1064* (2013.01); *A61N 5/1069* (2013.01); *A61N 2005/1061* (2013.01); *A61N 2005/1062* (2013.01)

(56) References Cited

U.S. PATENT DOCUMENTS

| | | | | |
|---|---|---|---|---|
| 2008/0109013 | A1* | 5/2008 | Fu et al. ....................... | 606/130 |
| 2009/0285366 | A1 | 11/2009 | Essenreiter et al. | |
| 2013/0287167 | A1* | 10/2013 | Gum .................... | A61N 5/1049 378/20 |
| 2014/0037173 | A1* | 2/2014 | Gum .................... | A61N 5/1049 382/131 |

FOREIGN PATENT DOCUMENTS

| | | |
|---|---|---|
| WO | 2008/063299 | 5/2008 |
| WO | 2010/143400 A1 | 12/2010 |

OTHER PUBLICATIONS

Yeung A R et al., "Tumor Localization Using Cone-Beam CT Reduces Setup Margins in Conventionally Fractionated Radiotherapy for Lung Tumors", International Journal of Radiation: Oncology Biology Physics, vol. 74, No. 4, Jul. 15, 2009, pp. 1100-11007, Pergamon Press, USA.

Wang Z et al., "Refinement of Treatment Setup and Target Localization Accuracy Using Three-Dimensional Cone-Beam Computed Tomography for Stereotactic Body Radiotherapy", International Journal of Radiation; Oncology Biology Physics,vol. 73, No. 2, Feb. 1, 2009, pp. 571,577, Pergamon Press, USA.

European Patent Office, Substantive examination,EP application No. 11700409, mail date: Oct. 28, 2015, pp. 1-10.

* cited by examiner

DETERMINATION OF A BODY PART POSITION DURING RADIATION THERAPY

This application is a national phase of International Application No. PCT/EP2011/050351 filed Jan. 12, 2011 and published in the English language.

The present application relates to the field of radiation therapy. In more detail, the application relates to the determination of the position of an anatomical body part (called treatment body part) relative to an arrangement of one or more positions (called beam positions) of a treatment beam. The determined position can be described in a reference system in which the arrangement is at rest, in particular relative to an intersection point of the treatment beams of the arrangement (in case the arrangement comprises more than one beam). Of course, it is for instance also possible to describe the determined position in another reference system, for instance reference system in which the anatomical body part is at rest or in any other reference system in which for instance the room (in which the treatment takes place) is at rest.

The present invention also relates to the field of control of the treatment beam. The treatment beam treats body parts to be treated which are referred to in the following as "treatment body parts". These body parts are in particular body parts of a patient, i.e. anatomical body parts.

The present invention relates to the field of medicine and in particular to the use of beams, in particular radiation beams in order to treat parts of the body. Ionizing radiation is in particular used for this purpose. In particular, the treatment beam comprises or consists of ionizing radiation. The ionizing radiation comprises or consists of particles (for example sub atomic particles or ions) or electromagnetic waves which are energetic enough to detach electrons from atoms or molecules and so ionize them. The treatment beam, in particular the treatment radiation is in particular used in radiation therapy (also called radiotherapy), in particular in the field of oncology. For the treatment of cancer in particular, parts of the body comprising the tumor are treated by using ionizing radiation. The tumor is an example for a treatment body part. The treatment beam is preferably controlled to pass through the treatment body part.

The arrangement of beam positions comprises (in particular consists of) at least one beam position, in particular a discrete set of beam positions or a continuous multiplicity (manifold) of beam positions. During treatment, a treatment beam in particular adopts the beam positions defined by the arrangement sequentially in particular in case there is just one beam source to emit a treatment beam. If there are several beam sources, beam positions can also be adopted simultaneously by the several treatment beams during the treatment. The arrangement of the at least one beam position which defines the at least one beam position relative to the treatment device, in particular during (actual) treatment (in particular during a treatment session, which is also called a fraction) is called actual arrangement. In particular, the actual arrangement has a point of intersection in which all treatment beams (in case of more than one) of the actual arrangement intersect. In particular, the determined position is described relative to the position of the intersection point, for instance in a reference system which has the intersection point in its origin. The intersection point corresponds in particular to an isocenter of the treatment device.

In particular, there is a defined planned relative position between a planned relative position of the treatment body part and a planned arrangement of beam positions. In particular a treatment planning (performed by a treatment planning system before the treatment, for instance based on computed tomographic images (called CT images)) results in the planned relative position between the treatment body part and the planned arrangement. In particular the actual arrangement is set to comprise the same number of beam positions as the planned arrangement. In particular in case the planned arrangement comprises two or more beam positions, the relative positions between the beam positions is set to be identical in the planned arrangement and in the actual arrangement.

It is an object of the present invention to determine the position of the treatment body part, in particular, the relative position (actual relative position) of the treatment body part relative to the actual arrangement in particular during a treatment session. Preferably also a correction of the position based on the determined actual relative position and the planned position is enabled. The actual relative position at a time called monitoring time is called herein monitoring tissue position.

The position of a part or a structure of the anatomical structure can in particular be represented (in particular described) by the position of the center (e.g. center of mass) of the part or of the structure.

The aforementioned problem is solved by the subject-matter of the independent claims. The dependent claims are directed to embodiments of advantage.

In the following advantageous features and advantageous embodiments of the invention are described.

The method in accordance with the invention is in particular a data processing method. The data processing method is preferably performed using technical means, in particular a computer. The computer in particular comprises a processor and a memory in order to process the data, in particular electronically. The calculating steps described are in particular performed by a computer. Steps of determining or calculating are in particular steps of determining data within the framework of the technical data processing method, in particular within the framework of a program. A computer is in particular any kind of data processing device. A computer can be a device which is generally thought of as such, for example desktop PCs or notebooks or netbooks, etc., but can also be any programmable apparatus, such as a mobile phone or an embedded processor. In particular, a computer can comprise a system (network) of "sub-computers", wherein each sub-computer represents a computer in its own right. A computer in particular comprises interfaces in order to receive data and/or to perform an analogue-to-digital conversion. The data are in particular data which represent physical properties and/or are generated from technical signals. The technical signals are in particular generated by means of technical detection devices and/or analytical devices.

Where data are "provided", this means that they are ready for use by the method or program in accordance with the invention. The data can achieve this state of being "ready for use" by for example being generated (e.g. by a CT or CBCT or MRT), in particular detected or captured (for example by analysis apparatuses) or by being input (for example via interfaces). The data can also achieve the state of being provided by being stored in a data storage (for example a ROM, RAM, CD and/or hard drive) and thus ready for use within the framework of the method or program in accordance with the invention. The expression "providing data" encompasses (within the framework of a data processing method) in particular that the data are determined by the data processing method or program. The meaning of "providing data" in particular encompasses also that the data are received by the data processing method or program, in particular to further process the data by the data processing method or program. Thus "providing data" can mean for instance to wait for a reception of data and to receive the data. The received data can be for instance inputted by the interface. "Providing data" can also mean that the data processing method or program performs steps to (actively) acquire the data from a data source, for instance a data storage (for instance ROM, RAM, data base, hard disk etc.) or via the interface (for instance from another computer or a network).

The advantageous data processing method is used for determining a position of the treatment body part which is to be treated by the treatment beam which is issued in accordance with the actual arrangement. Preferably, the position (called "actual relative position") is determined relative to the actual arrangement of at least one beam position and is therefore called "actual relative position". The actual relative position can change from time to time. The actual relative position which is given at a time called monitoring time is called herein monitoring tissue position. In particular the treatment body part is a soft tissue part (e.g. a tumor) of the anatomical structure of the patient. The term "soft tissue" means herein in particular that the soft tissue part is not part of a bony structure of the anatomical body of the patient.

Preferably, CBCT data are provided. The CBCT data describe a three-dimensional CBCT image of the anatomical structure. The CBCT image represents the anatomical structure at a time (called pre-alignment time) when the CBCT image was generated. The three-dimensional CBCT image represents the anatomical structure which includes the treatment body part and a bony structure. The term "bony structure" can encompass a complete set of all anatomical bony elements included in the anatomical structure and/or represented by the CBCT image or can just mean one or more parts of the "complete set". The one or more parts can be in particular landmarks, the position, in particular orientation of which is definable.

Landmark is a defined element of an anatomical body part which is always identical or recur with a high degree of similarity in the same anatomical body part of multiple patients. Typical landmarks are for example the tips of the transverse processes and/or dorsal process of a vertebrae. The treatment body part and the bony structure are represented by the CBCT image in a relative position to each other.

The abbreviation CBCT stands for cone-beam computed tomography and is in particular used in the field of image guided radiation therapy. Advantageously, the present invention is directed to this field of image guided radiation therapy (IGRT). A CBCT device (used for generating the CBCT images) is in particular arranged in a known position relative to the actual arrangement of at least one beam position. The actual arrangement of at least one beam position is in particular set in accordance with a treatment plan to adopt a particular position with respect to a treatment device which issues the treatment beam in accordance with the arrangement. Preferably, the relative position between the CBCT device and the treatment device is known which results in that the relative position between the actual arrangement and the CBCT device (and thus the CBCT image) is known.

The CBCT allows in particular to determine the position of the treatment body part with respect to the actual arrangement. In particular, deviations of the actual relative position of the treatment body part from the planned relative position (at the pre-alignment time) can be determined. In particular, the CBCT acquires a plurality of projections over the anatomical structure (volume of interest). In particular, the two-dimensional projections are reconstructed into a three-dimensional CBCT image (three-dimensional volume) in particular corresponding to data called pre-data (e.g. CT image data) by using reconstruction strategies (as proposed for instance by Feldkamp).

An advantage of the three-dimensional CBCT image is that it represents the soft tissue parts and therefore allows to register a three-dimensional CBCT image with respect to the three-dimensional image which was used for planning and which is described by the pre-data and which is called herein pre-image (as will be explained in more detail later). The planning is performed based on the pre-image. The planning results in a planned relative position of the (soft tissue) treatment body part relative to the arrangement. Thus, the three-dimensional CBCT image allows to align the treatment body part with the planned relative position and/or to confirm that the treatment body part is already in the planned relative position. Thus, the alignment results in that the treatment body part is in an aligned position which corresponds to the planned position. The alignment is in particular performed (just) before the treatment starts.

However, after the alignment, a patient can perform movements which result in a displacement of the treatment body part so that the treatment body part is no longer in the aligned position during the treatment.

There are radiotherapy systems which allow to repeatedly generate three-dimensional CBCT images or just two-dimensional x-ray images during a treatment session. This allows to compare the resulting three-dimensional images or the resulting two-dimensional images with the planning data (pre-data which describe the pre-image). The comparison is aimed to determine if the treatment body part is still aligned with the planned relative position or is displaced with respect to the planned relative position. The solution of the inventors allows to use the same type of radiotherapy system, however in a different manner as will be described in the following:

Preferably, x-ray image data are provided (in particular during treatment with a treatment beam) which describe at least one two-dimensional x-ray image of the anatomical structure (which includes the treatment body part). The at least one two-dimensional x-ray image represents the bony structure included in the anatomical structure (represented by the at least one two-dimensional x-ray image). The x-ray image data (and thus the at least one two-dimensional x-ray image) is generated after the three-dimensional CBCT image, i.e. at a point in time called monitoring time. This monitoring time is in particular during the treatment and in particular after the alignment while the pre-alignment time (when the three-dimensional CBCT image was generated) is in particular before the treatment and in particular before the alignment of the anatomical body part.

The x-rays which generate the two-dimensional x-ray image and in particular an x-ray device (which includes an x-ray source and an x-ray detector) has a particular (known) relative position relative to the treatment device and thus relative to the actual arrangement. Since the position of the x-ray device relative to one or more possible positions (in particular orientations) of the x-ray source and the x-ray detectors is known, the one or more positions of the x-ray source and x-ray detector is known. This one or more positions represent an example for describing information on the position of an imaging geometry and on the imaging geometry itself given when generating the two-dimensional x-ray image. Preferably x-ray geometry data describe this information. Preferably, x-ray data include the x-ray image data and the x-ray geometry data.

The x-ray geometry data preferably comprises information which allows the analysis image (x-ray image) to be calculated, given a known relative position between the imaging geometry and the analysis object (anatomical body part) to be analyzed by the x-ray radiation, if the object (anatomical body part) to be analyzed is known, wherein "known" means that the spatial geometry (size and shape) of the analysis object is known. This preferably means in particular that three-dimensional, "spatially resolved" information concerning the interaction between the analysis object (anatomical body part) and the analysis radiation (x-ray radiation) is known, wherein "interaction" means for example that the analysis radiation are blocked or partially or completely allowed to pass by the analysis object. The position, in particular orientation of the imaging geometry is in particular defined by the position of the (analysis apparatus) x-ray device, in particular by the position of the x-ray source and the x-ray detection and/or in particular by the position of the multiplicity (manifold) of x-ray beams which pass through the analysis object and which are detected by the x-ray detector. The imaging geometry describes in particular the geometry (size and/or shape) of this multiplicity (manifold). The shape is for instance a conus shape with a specific angle of inclination of the side walls of the conus with respect to a central line of the conus. The position of the imaging geometry (in particular the orientation) is in particular representable by the position of a x-ray beam being and passing through the center of this multiplicity and/or by a position of a geometric object (like a truncated conus) which represents the geometry of the multiplicity (manifold) of x-ray beams. Information concerning the above-mentioned interaction is preferably three-dimensionally known, for example from a three-dimensional CT, and describes the interaction in a spatially resolved way for (in particular all of the) points and/or regions of the analysis object. Knowledge of the imaging geometry (and of its position) in particular allows a position of a source of the radiation (for example, an x-ray source) to be calculated relative to an image plane (for example plane of an x-ray detector). With respect to the connection between three-dimensional analysis objects and two-dimensional analysis images, as defined by the imaging geometry, reference is made in particular to the following publications:

1. "An Efficient and Accurate Camera Calibration Technique for 3D Machine Vision", Roger Y. Tsai, Proceedings of IEEE Conference on Computer Vision and Pattern Recognition. Miami Beach, FLUID, 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Vol. RA-3, No. 4, August 1987, pages 323-344. See also http://www.cs.cmu.edu/~rgw/TsaiDesc.html
3. Publication by Ziv Yaniv, "Fluoroscopic X-ray Image Processing and Registration for Computer-Aided Orthopedic Surgery"
4. EP 08 156 293.6
5. U.S. 61/054,187

Preferably, x-ray data are provided which describe information (i.e. include information) on the position of the bony structure relative to the actual arrangement. This relative position is called herein "monitoring bone position". The monitoring bone position is the relative position of the bony structure at a point in time during treatment at which a monitoring of the position is performed by means of an x-ray device which generates at least one two-dimensional x-ray image. Preferably, at least two two-dimensional x-ray images from at least two different positions are generated. The x-ray data preferably include the x-ray image data and the x-ray geometry data. Preferably, the x-ray image data and the x-ray geometry data describe together the information on the monitoring bone position.

Preferably, the x-ray image data describe at least two two-dimensional x-ray images (in particular stereoscopic images) which allow the determination of a position of bony structure (shown in the x-ray images) for instance based on the x-ray geometry data. However, even in case of just one x-ray image, the position of the bony structure can be determined as described in the following.

In particular based on the at least two different x-ray geometries given when generating the at least two different x-ray images and based on the at least two different x-ray images, the position of the bony structure is determined relative to the actual arrangement at the monitoring time. In particular, additional information on the scaling of the x-ray image is available. That is in particular from the size of the bony structure displayed by the image, the actual size of the bony structure can be inferred if the position of the bony structure relative to the x-ray imaging geometry and/or x-ray device (in particular the distance to the x-ray source and/or x-ray detector) is known, the actual size being e.g. the size as represented by the pre-image. That is, based on the size of the bony structure represented (displayed) by the two-dimensional image and based on the known actual size of the bony structure (as for instance described by the pre-image), the position of the bony structure with respect to the x-ray imaging geometry can be inferred even from just one x-ray image.

According to an embodiment, the above-mentioned x-ray geometry data are provided. The x-ray geometry data can be included in the x-ray data. The x-ray geometry data can be received, e.g. from a data base. These x-ray geometry data describe a positional relationship between the arrangement (of at least one beam position) and the imaging geometry. In particular more than one (for instance two) x-ray images can be generated and/or there are in particular different imaging geometries given when generating the more than one x-ray images. In particular, an imaging geometry is assigned to each one of the more than one x-ray images so that there is more than one imaging geometry. Thus, there is at least one imaging geometry which respectively corresponds to at least one x-ray image.

Preferably, planning data are provided which describe the planned relative position between the treatment body part and the planned arrangement. The planning data are in particular generated based on pre-data which are for instance CT data or MRI data. The CT data describe a three-dimensional CT image of the anatomical structure. The MRI data describe a three-dimensional MRI of the anatomical structure. The pre-data are generated before the patient is positioned in the pre-alignment position. In particular, there is no known link between the position of the patient when generating the pre-data and when generating the CBCT data. The pre-data are generated at a point in time which is called herein "planning time". The planning time is before the pre-alignment time.

Preferably, the actual relative position of the treatment body part relative to the actual arrangement is determined. This position is called "monitoring tissue position". This position is determined as explained below and represents the position of the treatment body part relative to the actual arrangement at the monitoring time. Preferably, the determination is based on a position called "tissue-bone position" described by the CBCT image data. The tissue-bone pre-alignment position is the position of the treatment body part relative to the bony structure.

A CBCT device (which can also work as the x-ray device and) which is used to generate CBCT data (and optionally also the x-ray image data) has preferably a fixed position relative to the treatment device. Preferably, the actual arrangement has been set by means of the treatment device based on the planning data to have a fixed position relative to the treatment device. Thus, in particular, data called CBCT arrangement data are available (e.g. stored in a data base of the computer) which describe the relative position between the CBCT image and the actual arrangement, in particular between a reference system in which the CBCT image rests and the actual arrangement. In particular, the CBCT arrangement data allow to determine if the treatment body part is in the planned relative position (aligned position) at the time of generating the CBCT image, i.e. at the pre-alignment time. A correction of the position of the treatment body part can be performed if this is not the case.

Since the monitoring bone position is determined based on the x-ray data and since the tissue-bone pre-alignment position is determined based on the CBCT data (at the pre-alignment time), the monitoring tissue position can be determined (calculated) based on the CBCT data and the x-ray data under the assumption that the relative position between the treatment body part and the bony structure has not changed from the pre-alignment time to the monitoring time.

According to another embodiment, the monitoring bone position is determined based on the x-ray data and additionally based on CBCT position data describing the relative position between the CBCT image (and/or the anatomical structure represented by the CBCT image) and the actual arrangement. Based on the CBCT data and the CBCT position data and in particular based on the segmentation data, a position called bone CBCT position is determined. The bone CBCT position describes the relative position between the bony structure and the actual arrangement. The segmentation data describe the position of the bony structure within the CBCT image. Furthermore, the at least one x-ray image is matched, in particular registered with respect to the CBCT image. In order to achieve this, the CBCT image has to be transformed, i.e. has to undergo a translatorical and/or rotatorical transformation. The transformation is determined based on a relative position between the imaging geometry and the x-ray device present when generating the at least one x-ray image and the position of the CBCT image. The relative position being described by data called CBCT x-ray data. The relative position can be for instance determined by using a model visible in both the CBCT and the at least one x-ray image and by generating x-ray images and a CBCT image from this model and by using the known structure and/or geometry of this model (which can be a cube). The relative position can also be determined by using an irregular model or just the bony structure of the patient and by detecting markers attached to the x-ray device by means of a navigation system. The latter solution is described in EP 2 119 397 of the present applicant which is herewith incorporated by reference. Based on this transformation, the monitoring bone position is determined. The monitoring bone position is determined based on the change of position described by the transformation and based on the bone CBCT position.

As described above, preferably at least one of x-ray geometry data and/or CBCT position data are provided in order to determine the monitoring bone position. Thus, the x-ray data which describe information on the monitoring bone position can include just the x-ray image data or the x-ray image data and the x-ray geometry data. If they only include the x-ray image data, at least then preferably the CBCT position data are provided for determination of the monitoring bone position. According to a further embodiment, both the x-ray geometry data and the CBCT position data are provided. In particular in the latter case, it is possible to determine the monitoring bone position in two different ways which allows for a checking of the reliability of the determination.

Preferably, the patient is already placed with respect to the treatment device at the pre-alignment time. In particular, only a smaller movement of the patient with respect to the treatment device is necessary after the pre-alignment time in order to align the treatment body part with respect to the actual arrangement based on the CBCT data. Thus, it is unlikely that there is a major shift between soft tissue structures like the treatment body part and the bony structure.

According to a preferred embodiment, the monitoring tissue position is determined by generating digitally reconstructed radiographs (called "DRRs") from the three-dimensional CBCT image. Preferably, at least one two-dimensional DRR is determined which matches the at least one two-dimensional x-ray image. In order to generate the DRRs, imaging geometries are simulated. If a "DRR" matches an x-ray image, the simulated imaging geometry (used to generate the DRR) is called matching imaging geometry. To each of the at least one two-dimensional x-ray image corresponds a respective matching imaging geometry. The matching of a DRR with an x-ray image is preferably performed based on (in particular only based on or predominantly based on) the bony structure such that the bony structure shown in the DRR and shown in the x-ray image match with each other, in particular achieve a best match. In particular, other parts of the anatomical structure which are not part of the bony structure are weighed less in the matching process than the bony structure. In particular, a segmented bony structure is used for matching, in particular only the bony structure is used for matching. Preferably, there are at least two x-ray images which are respectively to be matched with one of the simulated DRRs. Preferably, a plurality of DRRs are generated and the matching DRRs are selected out of the plurality of DRRs.

Due to the simulation, the relative position (in particular orientation) between the at least one matching imaging geometry and the anatomical structure represented by the three-dimensional CBCT image is known. If assuming that the three-dimensional image adopts virtually the same position in space as the anatomical structure (which it represents), it can also be said that the relative position between the at least one matching imaging geometry and the three-dimensional CBCT image is known due to the simulation. Based on the relative position between the (at least one) matching imaging geometry and the anatomical structure (three-dimensional CBCT image) and the (known) relative position between the anatomical structure (three-dimensional CBCT image) and the actual arrangement (at the pre-alignment time), the relative position between the matching imaging geometry and the actual arrangement at the pre-alignment time can be determined. In case this relative position differs from the relative position between the (at least one) x-ray imaging geometry and the actual arrangement at the monitoring time, this is due to a positional change of the anatomical structure. This positional change corresponds to an imaging geometry difference which will be explained in the following.

If there had been a positional change (e.g. rotational and/or translatoric change) of the bony structure from the pre-alignment time to the monitoring time, the position of the at least one x-ray imaging geometry relative to the actual arrangement at the monitoring time will differ from the corresponding at least one position of the at least one matching imaging geometry relative to the actual arrangement at the pre-alignment time. This difference is the above-mentioned imaging geometry difference. Thus, to each of the at least one x-ray imaging geometries corresponds one imaging geometry difference. The imaging geometry difference represents the positional change of the bony structure, in case the bony structure was used for the above-mentioned matching process. The image geometry difference, in particular the positional change can be zero or larger than zero.

However it is also possible to determine the positional change of the treatment body part from the pre-alignment time to the monitoring time based on a predefined relationship which can be described by a predefined function. This predefined function describes in particular the change of position of the treatment body part in dependence on the change of position of the bony structure and/or in dependence on the pre-alignment difference (which is compensated by the alignment).

The predefined relationship describes a relationship between a first relative position and a second relative position. The first relative position is the position between the treatment body part and the bony structure at a pre-alignment time and is identical with the tissue-bone pre-alignment position. The second position describes the position between the treatment body part and the bony structure at the monitoring time. This second position is called tissue-bone monitoring position. The tissue-bone monitoring position is in particular not known. The predefined relationship is in particular constituted to allow the determination of the tissue-bone monitoring position based on the tissue-bone pre-alignment position. According to the predefined relationship, the first relative position is in particular identical with the second relative position. Thus, the second relative position can be set to be identical with the first relative position. Of course, there are other examples how to implement the step of setting. In particular, the step of setting the second position can be implemented by a step of determining the second relative position. For instance the predefined relationship can be described by a lookup table or by a mathematical formula and the second relative position is determined based on the lookup table or the formula. The lookup table and the formula can be stored in a database and the method accesses the database for setting (determining) the second relative position.

According to an embodiment, the step of setting, in particular determining the tissue-bone monitoring position based on the tissue-bone pre-alignment position and the predefined relationship is identical with a step of using the tissue-bone pre-alignment position as the tissue-bone monitoring position. In particular, the predefined relationship is a relationship of identity, that is the predefined relationship of identity can be described by a predefined function of identity. According to this function of identity, the treatment body part performs a positional change which is identical with the positional change of the bony structure. In other words, the monitoring tissue position can be determined based on the determined at least one imaging geometry difference under the assumption that the relative position between the treatment body part and the bony structure has not changed from the pre-alignment time to the monitoring time. That is the predefined function describes the anatomical structure in particular to be rigid. However, the predefined function can also describe non-rigid properties of the anatomical structure, in particular reflects positional changes of the bony structure. As mentioned above, the predefined relationship of identity describes that there is no positional change between a first relative position between the treatment body part and the bony structure at the pre-alignment time and a second relative position between the treatment body part and the bony structure at the monitoring time. That is the predefined relationship described by the predefined function is that the first relative position is identical with the second relative position. The predefined relationship of identity is a good approach if the positional change of the treatment body part from the pre-alignment time to the alignment time is small, in particular if the positional change is just a translatoric change (horizontally and/or vertical change) and not a rotational change. Tilting of a patient body can cause a compression or an expansion of the body due to the effects of gravity. Thus, the relative position between the treatment body part and the bony structure can change in dependence on the change of position of the patient body. Thus, in particular, the predefined relationship can depend on the pre-alignment difference. According to an embodiment, the predefined function accesses a look-up table in which positional changes of the treatment body part relative to the bony structure in dependence on a change of position of the bony structure and in particular depending on the kind and amount of change (rotational and translatoric) is stored. In particular, the predefined function can be a function depending on the positional change of the bony structure from the pre-alignment time to the alignment time and can be a function on the relative position between the treatment body part and the bony structure at the pre-alignment time. In particular, it can be defined that the larger distance between the bony structure and the treatment body part, the greater is the influence of rotation of the treatment body part on the change of relative position between the treatment body part and the bony structure. In order to generate the aforementioned look-up table, a CT of the patient can be generated for different positions of the patient relative to the field of gravity in order to gather data about the change of position between the bony structure and the treatment body part. In this way, it is possible to determine the relative position between the bony structure and the treatment body part in dependence on the rotational position of the treatment body part relative to the field of gravity. In the following description it is assumed in an unlimiting manner that the first relative position is equal to the second relative position.

In particular, the at least one image geometry difference describes the positional change of the bony structure relative to the actual arrangement from the pre-alignment time to the monitoring time.

As indicated above, the monitoring tissue position can be determined by determining the positional change of the tissue-bone pre-alignment position (e.g. represented by a vector, the base of which is at the bony structure and the tip of which is at the treatment body part) relative to the actual arrangement. The monitoring tissue position can be in particular determined by positioning the base of the changed vector at the monitoring bone position. Then the tip of the changed vector is at the monitoring tissue position. Alternatively the monitoring tissue position can be determined by determining the positional change of the anatomical structure represented by the CBCT image from the pre-alignment time to the monitoring time relative to the actual arrangement (while assuming that the anatomical structure behaves as described by the predefined function, i.e. in particular while assuming that the anatomical structure is rigid). Thus, in other words, according to the latter embodiment, a new position of the anatomical structure and thus of the three-dimensional CBCT image (which represent this structure) relative to the actual arrangement is determined based on the at least one image geometry difference. As mentioned above, the three-dimensional CBCT image is assumed herein to have a (virtual) spatial position which is identical with the spatial position of the anatomical structure which it represents. The position of the treatment body part within the newly positioned anatomical structure and thus within the three-dimensional (CBCT image (called new CBCT image) and relative to the actual arrangement represents the monitoring tissue position. The newly positioned anatomical structure is in particular assumed to be identical (rigid property) with the anatomical structure represented by the three-dimensional CBCT image (also called shortly "CBCT image") at the pre-alignment time, however, the newly positioned anatomical structure and thus the new CBCT image can have a position (relative to the actual arrangement) which is different from the position of the anatomical structure (and thus of the CBCT image) at the pre-alignment time. The monitoring bone position is preferably determined based on the position of the bony structure within the newly positioned anatomical structure and based on the relative position of the newly positioned anatomical structure relative to the actual arrangement.

In other words, the monitoring tissue position is determined based on the monitoring bone position and based on a predefined relationship between the first relative position (at the pre-alignment time) and the second relative position (at the monitoring time). As mentioned above, this predefined relationship is described by the predefined function. The predefined relative position is in particular assumed to be the same as in the CBCT image of the pre-alignment time. Since the aforementioned matching has been performed based on the bony structure while finally the monitoring tissue position is determined based on the position of the treatment body part within the newly positioned anatomical structure, the determination of the monitoring tissue position is based on the predefined relationship. The predefined relationship can be preferably described by the assumption that the relative position between the treatment body part and the bony structure has not changed from the pre-alignment time to the monitoring time, i.e. is as represented by the CBCT image.

The position of the treatment body part within the anatomical structure and thus within the CBCT image (and in particular relative to the bony structure) at the pre-alignment time is preferably described by using segmentation data. The segmentation data describe in particular the relative position of the segmented treatment body part relative to the bony structure in the anatomical structure and thus within the CBCT image. The segmentation data describe in particular the position of the segmented treatment body part and/or of the bony structure, for instance in a reference system in which the anatomical structure and the CBCT image is at rest. The segmentation data can for instance be generated by a (non-rigid) matching of a three-dimensional (in particular segmented) pre-image (for instance a CT image) with the CBCT image. The pre-image is in particular used for planning and the treatment body part is identified (in particular segmented) during the planning process which is performed based on the pre-image.

In the previous embodiment described above, the monitoring tissue position is determined by generating DRRs and by matching (in particular registering) the DRRs with the two-dimensional x-ray images. In this way, the monitoring tissue position can be determined based on information on the monitoring bone position described by the x-ray data. This is also possible according to another embodiment. According to this another embodiment which can be combined with the previous embodiment, the monitoring tissue position is determined based on the x-ray data without the above described matching of DRRs. For instance several x-ray images are generated from different orientations and the x-ray imaging geometry (given when generating these x-ray images) is known by the x-ray geometry data. Then, the monitoring bone position can be determined based on the x-ray data. For instance, the x-ray images (corresponding to different x-ray imaging geometries) are displayed on a screen and data called bony structure data are received by the method. The bony structure data describe the position and/or geometry of the at least part of the bony structure in at least one of the x-ray images. For instance an operator or a pattern recognition algorithm identifies at least a part of the bony structure on the screen by means of a mouse or a pen for generating the bony structure data. Based on the received bony structure data, then the monitoring bone position is determined. Furthermore, under the assumption that the tissue-bone pre-alignment position is not changed from the pre-alignment time to the monitoring time, the monitoring tissue position can be determined based on the monitoring bone position determined in the previous step. The monitoring bone position represents the position of the bony structure. Furthermore, the tissue-bone pre-alignment position (described by the CBCT data) describe the relative position between the treatment body part and the bony structure For instance, the bony structure data describe the position of one or more particular bone elements (e.g. landmarks) part in the at least one x-ray image and the tissue-bone pre-alignment position describers the relative position of the treatment body part and the one or more particular bone element. Furthermore, based on the x-ray geometry data and the position of the one or more particular bone elements (e.g. landmarks) in one or more of the x-ray images, the position of the one or more particular bone elements relative to the arrangement (i.e. the monitoring bone position) can be determined. Then, based on the monitoring bone position and the set tissue-bone monitoring position, the monitoring tissue position can be determined.

In particular, the aforementioned segmentation data describe the tissue-bone pre-alignment position. As mentioned before, the segmentation data can be generated during planning and by matching the "segmented" pre-image with the CBCT image.

As mentioned above, the tissue-bone pre-alignment position is preferably provided based on the above-mentioned segmentation data. As mentioned above, the segmentation data can be determined based on the pre-data and the CBCT data. The tissue-bone pre-alignment position can be determined automatically based on the segmentation data. Alternatively or additionally, the tissue-bone pre-alignment position can be received by the data processing method. In particular, the data processing method outputs the CBCT image (for instance on a screen) and an operator indicates the position of the bony structure and the position of the treatment body part. The indicated positions are received by the data processing method and describe the tissue-bone pre-alignment position. The provided tissue-bone pre-alignment position is preferably used to determine the monitoring tissue position.

As mentioned before, according to an advantageous embodiment, the segmentation data are provided which describe the position of the segmented treatment body part and/or of the segmented bony structure in the CBCT image and/or the relative position between the treatment body part and the bony structure. This segmentation data can be generated during a planning process. The planning process results in particular in planning data which describe the planned relative position between the treatment body part and the arrangement. According to a preferred embodiment, providing the planning data represents a further step of the data processing method. The step of providing planning data is in particular a receiving step. The provision of the planning data enables the data processing method to determine a difference between the monitoring tissue position and the planned relative position.

According to a further embodiment, the segmentation data describe the segmented bony structure in the CBCT image. This can be done for instance by an automatic segmentation algorithm or by means of a user which identifies the bony structure in the CBCT image. In this way, the segmentation data describe in particular a three-dimensional model of the bony structure. This three-dimensional model of the bony structure (based on the CBCT image) is then preferably matched, in particular registered with respect to the at least one x-ray image. Since there is a defined positional relationship between the three-dimensional model of the bony structure and the CBCT image, the new position of the anatomical structure and thus of the three-dimensional CBCT image relative to the actual arrangement can be determined since the relative position between the three-dimensional model and the actual arrangement is known due to the above described matching (in particular registration) step. The monitoring tissue position can then be determined based on the position of the treatment body part within the registered (newly positioned) anatomical structure and based on the relative position of the registered (newly positioned) anatomical structure relative to the actual arrangement.

The above-mentioned embodiment is a feature-based embodiment, i.e. the matching, in particular registration process is based on features of the three-dimensional CBCT image, in particular based on features of the bony structure (in particular its geometry, i.e. size and/or shape). Instead of the three-dimensional model which represent the bony structure it is also possible to use two-dimensional models of the bony structure which represent a surface of the bony structure. Then the two-dimensional model of the bony structure is matched, in particular registered with respect to one-dimensional features, in particular contours (outlines) of the bony structure represented by the x-ray image. Thus, generally a model (in particular three-dimensional or two-dimensional model) of the bony structure is generated from the CBCT image which in particular represents at least a part of two- and/or three-dimensional features (in particular geometry features) of the bony structure. Based on this model a matching, in particular registration process is performed with respect to the two- and/or one-dimensional features of the x-ray image. Based on the registered model, the monitoring tissue position can be determined. This determination is in particular performed by determining the position of the CBCT image based on the position of the matched (registered) model.

As mentioned above, the planning data are preferably provided based on the pre-image. The pre-image is described by the pre-data. The pre-image represents a three-dimensional image of the anatomical structure which includes the treatment body part. The pre-data are generated before generating the CBCT-data. In particular, a spatial relationship between the pre-image and the actual arrangement is unknown (i.e. not provided to the data processing method). However, as mentioned above, preferably the planning data describe the relative position between the pre-image and the planned arrangement, in particular the planned relative position between the treatment body part identified (in particular segmented) in the pre-image relative to the planned arrangement. In accordance with an advantageous embodiment, the data processing method controls the position of the treatment body part so that an actual position between the treatment body part and the actual arrangement becomes identical with the planned relative position. The control is performed based on the determined monitoring tissue position. In particular, if there is a deviation between the monitoring tissue position and the planned relative position, a control is performed in order to change the actual relative position and to reduce, in particular to minimize, in particular to zero this deviation.

As mentioned above, a patient is preferably first analyzed in order to generate the pre-data (e.g. by using a CT or MRI). The generation of the pre-data can be on a different day and in particular in a different room so there is in particular no known spatial relationship between the reference system in which the pre-image is described and the position of the actual arrangement. The position of the actual arrangement is set relative to a patient placed relative to the treatment device within the treatment system (for instance on a couch of the treatment system). The placement is in particular performed by a medical staff member who tries to align the patient in accordance with the planning, in particular based on landmarks visible on the body of the patient. Since generally the treatment body part is inside the patient, the member of the medical staff is not aware if the placement is correct. Therefore, preferably, the abovementioned three-dimensional CBCT images are generated after the placement (pre-alignment) of the patient with respect to the treatment device at the pre-alignment time. Preferably, the relative position between a reference system within which the actual arrangement is set and a reference system within, which the three-dimensional CBCT image is described, is known. Thus, preferably the CBCT arrangement data are provided to the method according to an embodiment of the invention. The CBCT arrangement data describes the relative position between the three-dimensional CBCT image and the actual arrangement at the time of generating the CBCT image, i.e. at the pre-alignment time. This position is called pre-alignment CBCT position. Since the anatomical structure is described by the CBCT image, the CBCT arrangement data also describe the relative position between the anatomical structure and the actual arrangement at the time of generating the CBCT image. Preferably, based on the pre-alignment CBCT position (described by the CBCT arrangement data) and based on the position of the treatment body part with respect to the CBCT image (within the CBCT image and thus within the anatomical structure) described by the segmentation data, a position called pre-alignment tissue position is determined. The pre-alignment tissue position is the relative position between the treatment body part and the actual arrangement at the pre-alignment time. Performing an alignment between the pre-alignment time and the alignment is an optimal and preferred but not an obligatory step.

Preferably, the three-dimensional CBCT image and the three-dimensional pre-image is matched in accordance with an advantageous embodiment. The matching is preferably performed based on (in particular only based on or predominantly based on) the treatment body part, i.e. so that the treatment body part shown in the CBCT image and the treatment body part shown in the pre-image match with each other in particular achieve a best match. In particular other parts of the anatomical structure which are not the treatment body part are weighed less in the matching process than the treatment body part. In particular, the segmented treatment body part, in particular only the segmented treatment body part is used for matching. The matching is in particular a rigid matching that is the image, in particular the segmented treatment body part is not deformable. Based on the matched images, a difference between the planned relative position and the pre-alignment tissue position can be determined. This difference is called pre-alignment difference.

Of course, if there is no pre-alignment difference, no control for changing the relative position between the treatment body part and the actual arrangement is performed according to an embodiment. If there is a pre-alignment difference, then preferably (but not obligatory) a control is performed (at least in case a predefined threshold for the difference is passed). The control is preferably performed based on the determined pre-alignment difference. Thus, in accordance with an advantageous embodiment, in dependence on the pre-alignment difference, control data (called alignment control data) are determined. The term "in dependence on" means in particular that this control is performed if there is a difference in particular if the difference is above a predetermined threshold (which can be zero or more) and means in particular that in case of a control the control is based on the determined pre-alignment difference.

The determined alignment control data are for controlling the actual relative position. The control is optimal. The control is performed such that the difference between the planned relative position and the actual relative position after the control is smaller than the pre-alignment difference, in particular the difference is zero. In other words, the alignment control data are constituted to control the actual relative position of the treatment body part to correspond to the planned relative position. Preferably, according to an advantageous embodiment, the alignment control data are outputted in order to achieve the control before the monitoring time, in particular before the treatment of the treatment body part by means of the treatment beam starts. In particular, at the monitoring time, it is assumed that the position of the treatment body part has been (already) controlled in accordance with the alignment control data.

According to a further advantageous embodiment, control data (called x-ray based control data) are determined. These control data are for controlling the position of the treatment body part based on the x-ray data. In particular in case the monitoring tissue position deviates from the planned relative position (in particular by more than a predetermined threshold), the x-ray based control data are determined, in particular output to control the position of the treatment body part.

According to the above-described advantageous embodiments, data (called alignment position data) are provided. The alignment position data describe the relative position between the three-dimensional CBCT image and the actual arrangement at a point in time called alignment time. This position is called alignment position since it preferably relates to the position after the aforementioned alignment is performed based on the CBCT image. That is, in other words, the alignment position is in particular the relative position between the treatment body part and the actual arrangement after outputting the alignment control data and after controlling the position of the treatment body part in accordance with the control data. In particular, the alignment position is the position of the treatment body part relative to the actual arrangement at a point in time (the alignment time) before the monitoring time and/or after the pre-alignment time, in particular after controlling the position of the treatment body part in accordance with the alignment control data. In particular, there is an extended time difference between the alignment time and the monitoring time which can result in a displacement of the treatment body part with respect to the bony structure, for instance due to an (unintended) movement of the patient.

The alignment position data can be determined based on the control data which describe a positional displacement of the treatment body part and/or based on the determined pre-alignment difference (in case the control data are assumed to fully compensate the pre-alignment difference) and based on the pre-alignment position data described above. In case there is no pre-alignment difference, the alignment position data are assumed to correspond to the pre-alignment position data.

According to an embodiment, the predefined relationship can be determined as a function of the pre-alignment difference, in particular in case the couch is controlled in order to compensate the pre-alignment difference. In that case, the position of the patient is changed which can cause a change of position between the treatment body and the bony structure. That is, the tissue-bone monitoring position can become different from the tissue-bone pre-alignment position due to the change of position of the patient. Since the change of position of the patient is dependent on the pre-alignment difference, the predefined relationship can be dependent on the pre-alignment difference.

Advantageously, a difference (called correction difference) between the determined monitoring tissue position and the planned relative position (provided by the planning data) is determined. Preferably control data (called x-ray based position control data) are determined in dependence on the determined correction difference. The x-ray based position control data are for controlling the relative position between the actual arrangement and the treatment body part so that this relative position corresponds to (in particular is identical with) the planned relative position. For the determination of the x-ray based position control data, preferably the position of the treatment body part at the monitoring time is considered. To this end, preferably the above-mentioned alignment position data are used which describe the alignment position. In other words, the x-ray based position control data cause a control which compensates a difference between the alignment position and the monitoring tissue position.

The above-mentioned term "in dependence on the correction difference" means in particular that the x-ray based position control data are determined and/or outputted only if the correction difference exceeds a predetermined threshold. This threshold can be zero or can be above zero. The term "in dependence on" means in particular that the correction difference is only determined and/or only outputted if the difference is above zero.

Advantageously the method comprising a step of generating control data (called x-ray imaging control data) which are constituted to cause the generation of the x-ray data (in particular of the x-ray image data) after a (regular or irregular) period of time or in response to an external signal.

In particular during this period of time, there is a treatment of the treatment body part by the treatment beam.

Preferably the generation of the x-ray images is repeated and the output of the x-ray based position control data is also repeated. In particular outputting the x-ray imaging control data and outputting the x-ray based position control data are repeated. In particular, the x-ray based position control data are determined based on the lastly determined monitoring tissue position (which was determined based on the lastly received x-ray data (in particular x-ray image data)). These steps are in particular repeated during treatment of the treatment body part in order to (repeatedly) correct the position of the treatment body part to be in line with the planned relative position.

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention is also directed to radiotherapy system which comprises the above-mentioned computer. Furthermore, the radiotherapy system comprises preferably the treatment device. Preferably, the treatment system comprises a couch for placing the patient thereon. The treatment device is preferably constituted to treat the treatment part if the patient is placed on the couch for treatment. In particular, the treatment device is constituted so that the relative positions between the beam positions relative to the treatment device are controllable (in particular settable) to that an arrangement of beam positions can be set, the relative positions of the set arrangement corresponding preferably to (in particular are identical with) with the relative positions between the beam positions of the planned arrangement. In particular the couch and the treatment device are constituted so that the relative position between the set arrangement of beam positions and the treatment body part is changeable.

Preferably the treatment system comprises a CBCT-device. The CBCT-device is constituted to generate the three-dimensional CBCT images. In particular, the computer comprises a database within which the relative position between the CBCT image generated by the CBCT-device and a reference system of the treatment device is known. Preferably, the relationship between a reference system within which the actual arrangement is set and the reference system of the CBCT image is stored in the data base and/or is determinable based on the data stored in the database of the computer and based on data describing the set actual arrangement.

According to an embodiment, the x-ray images are generated by means of the CBCT-device. According to another embodiment, an x-ray device (which is independent from the CBCT-device) is part of or associated with/attached to the radiotherapy system and is used for generating the two-dimensional x-ray images. Preferably, the database of the computer stores a positional relationship between the x-ray imaging geometry (or x-ray imaging geometries) and reference system of the CBCT-image and/or a reference system within which the position of the actual arrangement is set. Preferably, after setting of the arrangement, the relative beam positions defined by the arrangement are fixed with respect to each other but, according to an embodiment, the position of set arrangement can be determined with respect to the treatment device. The actual arrangement is set in particular in accordance with control data (called arrangement control data which are provided (in particular received)). The arrangement control data can be set by an operator to comply as best as possible with the planned relative position under the assumption of an assumed position of the treatment body part (after placing the patient on the couch). The arrangement control data defines a position of the actual arrangement in the reference system of the arrangement.

According to an embodiment, the position of the couch is changeable by means of the alignment control data and/or x-ray based control data. Additionally or alternatively, the position of the actual arrangement within the reference system of the arrangement is changeable based on the alignment control data and/or the x-ray based position control data. Thus, the position of the treatment body part relative to the actual arrangement can be changed by changing the position of the couch and/or by changing the position of the actual arrangement within the reference system of the treatment device.

In particular, control signals are issued by the computer to the couch and/or to the treatment device for changing the relative position between the couch and the reference system of the treatment device.

In the following detailed description of embodiments, further advantageous features are disclosed. Different features of different embodiments can be combined.

Figure 1:
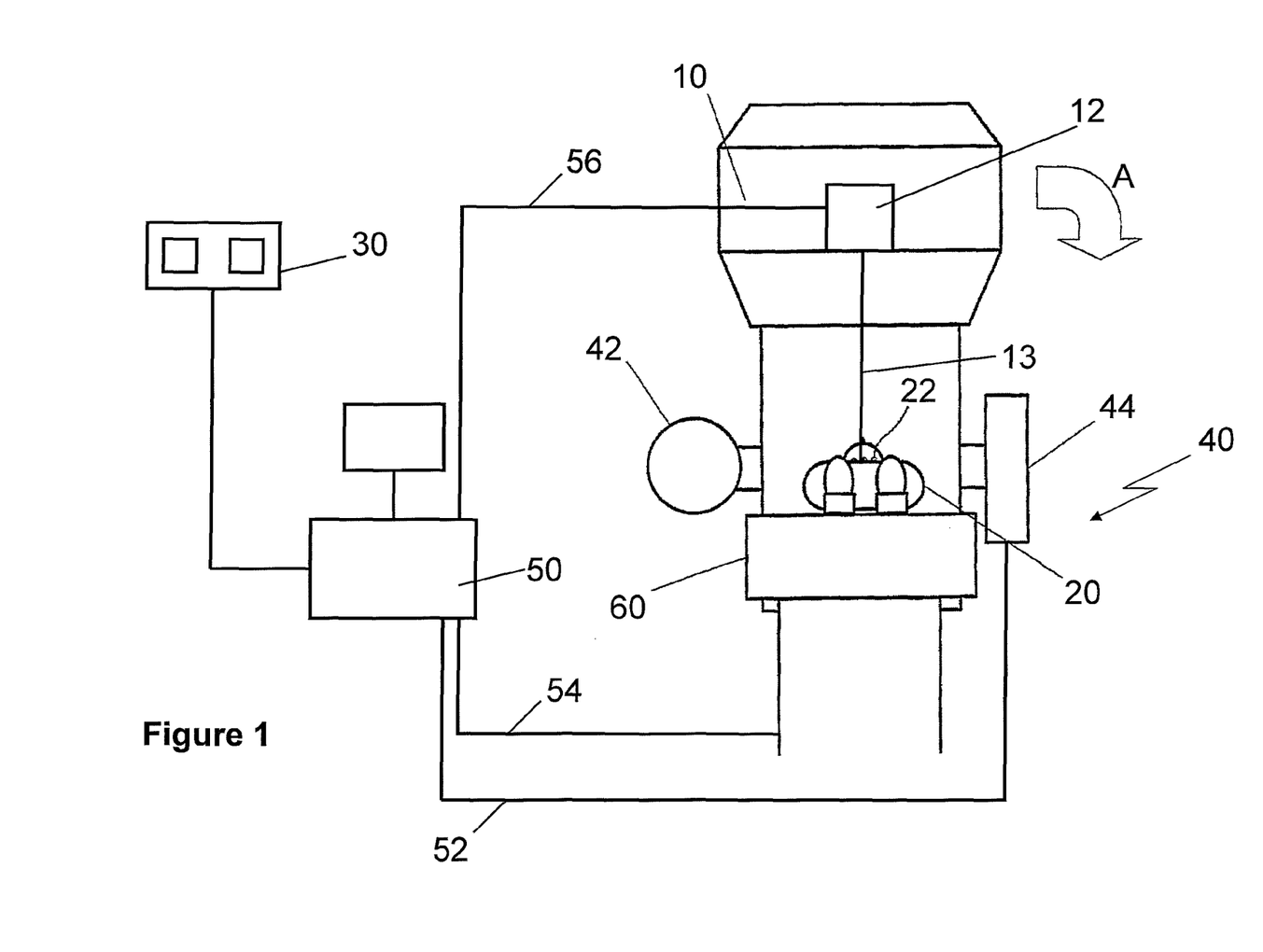
FIG. 1 shows schematically a treatment system in accordance with the invention.

FIG. 1 shows a radiotherapy system in accordance with an embodiment of the invention. A treatment device 10 includes a beam source 12 which issues a treatment beam 13 and which can be movable in a direction A relative to the treatment device 10. In the example given, the treatment device 10 has a fixed position in the room. The treatment beam 13 hits a patient 20. On the surface of the patient 20, optical markers 22 are attached. The position of the optical markers 22 can be detected by means of a camera 30 of a navigation system used in image guided surgery. The camera 30 is connected with a computer 50 on which a program for image guided surgery is running in order to determine the position of the markers 22. Preferably, the patient 20 is positioned so that the determined position of the markers 22 corresponds to the planned relative position of the markers 22.

The radiotherapy system preferably comprises a CBCT device 40 which comprises an x-ray source 42 and an x-ray detector 44. Thus, the CBCT device 40 also works as the x-ray device used for monitoring the position of the treatment body part at the monitoring time. Preferably, the x-ray source 42 and the x-ray detector 44 are rotatable around the patient 20 in order to generate the plurality of x-ray images of the patient from different directions. Based on this plurality of the images, the CBCT image (and thus the CBCT data) is generated by the computer 50 which is connected to the detector 44 by a signal line 52. In particular, the plurality of positions of the x-ray detector 44 and x-ray source 42 (adopted during generation of the CBCT image) is known in the reference system of the CBCT image for generating the CBCT image based on this knowledge.

In particular two x-ray images from different directions are generated at the monitoring time in order to generate the x-ray image data.

Preferably, the computer 50 is constituted to control the position of a couch 60 on which the patient 20 is lying by means of a signal line 54 and the position or aiming of the treatment beam source 12 by means of a signal 56. Furthermore, the computer 50 is preferably constituted to initiate the generation of the CBCT image by means of the signal line 52 and of preferably at least two and less than five images from different directions by means of the device 40 at the monitoring time. Preferably, two stereoscopic images are generated by means of the x-ray device 40 while preferably more than 50 x-ray images are generated in order to determine the CBCT image.

Figure 2:
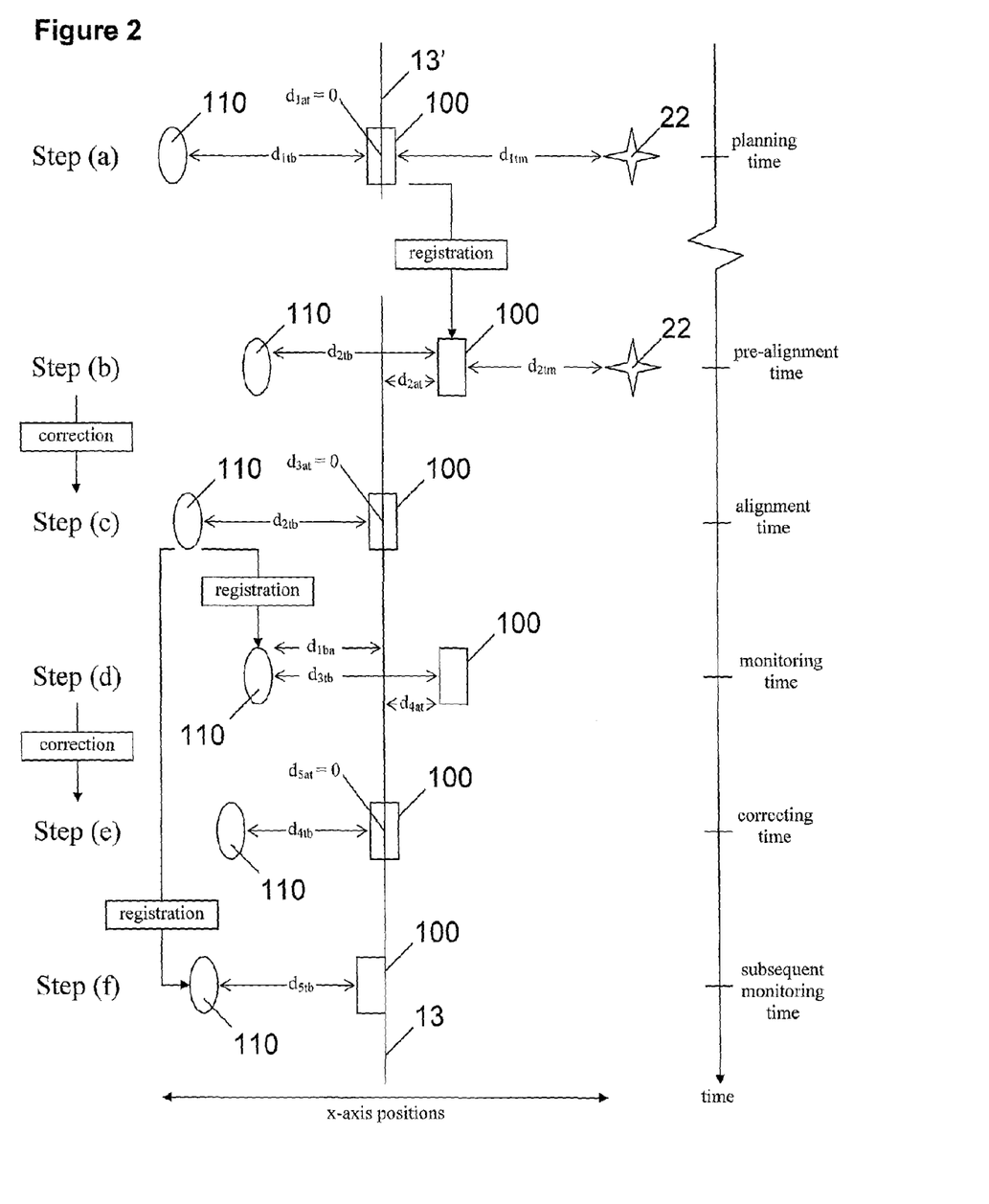
FIG. 2 shows principles of the determination and correction of the position of the treatment body part.

FIG. 2 shows different steps before and during treatment of a patient with a treatment beam in a schematic one-dimensional manner. FIG. 2a shows a treatment body part 100 in an rectangular shape and a bony structure 110 in a round shape in different positions along an x-axis of a first reference system (step a)) in which the planned arrangement is at rest and a second reference system (steps b) to f)) in which the actual arrangement is at rest. Furthermore, the reference sign 22 refers to a landmark or marker in a star shape. The step a) relates to the time of planning and generation of a pre-image (in particular CT image). At the time of FIG. 2a, the bony structure 110 and the treatment body 100 have a relative position marked by $d_{1tb}$. This relative position is represented by the distance $d_{1tb}$ which represents the distance between the soft tissue (i.e. the treatment body part, e.g. the tumor) 100 and the bony structure (e.g. a bone) 100. Furthermore, there is a relative position between the treatment body part 100 and the landmark or marker 22. This relative position is described as a distance $d_{1tm}$. At the time of planning, the position of the treatment beam 13' relative to the treatment body part 100 is planned. The position of the planned treatment beam 13' represents the position of the planned arrangement in FIG. 2a. Furthermore, a relative position between the treatment body part 100 and a landmark or marker 22 visible or touchable at the surface of the body is noted $d_{1tm}$. Furthermore, the planned relative position, the relative position between the treatment body part and the planned arrangement 13' is noted (i.e. stored as planning data).

FIG. 2b refers to a later point in time where the patient is in particular placed at a different couch as in case of FIG. 2a. The patient is in the so called "pre-alignment position" (at the pre-alignment time). The pre-alignment position has been chosen under the assumption that the relative position between the treatment body part 100 and the landmarks or marker 22 remains unchanged from the planning time to the pre-alignment time. However, as shown in FIG. 2b, the relative position $d_{2tm}$ between the treatment body part 100 and the landmark or marker 22 has changed. This results in that the treatment body part is displaced with respect to the actual arrangement (represented by the actual treatment beam 13) by a pre-alignment distance $d_{2at}$, i.e. the relative position between the actual arrangement 13 and the treatment body part 100 does not correspond to the planned relative position $d_{1at}$ described in FIG. 2a. The planned relative position $d_{1at}$=0. Furthermore, the relative position between the treatment body part 100 and the bony structure 110 $d_{2tb}$ shown in FIG. 2b can be different from that shown in FIG. 2a. The actual arrangement 13 is set in accordance with the planning data under the assumption that the treatment body part 100 is set correctly and/or under the assumption that the relative position between the planned arrangement 13' and the landmark or marker 22 has to be identical with the relative position between the actual arrangement 13 and the marker or landmark 22 at the pre-alignment time. Thus, as a result of the pre-alignment, the actual arrangement 13 for instance can be set in a defined position with respect to at least one of the following: the treatment device 10, the landmark or marker 22, the couch 60, a reference system of the CBCT image and the one or more positions of the x-ray imaging geometry. The actual arrangement describes in particular a number of, in particular plurality of positions of the beam source 12 with respect to at least one of the following: the treatment device 10, the marker or landmark 22, the couch 60, a reference system of the CBCT image, and the one or more positions of the x-ray imaging geometry. This arrangement can be a multiplicity (manifold) of continuously or discretely adopted positions.

At the pre-alignment time shown in FIG. 2b, preferably a CBCT image is generated. Preferably, the relative position between the actual arrangement 13 and the CBCT image is known. The term "is known" means herein in particular that information representing the knowledge is stored in the data base and accessible by the data processing method. Preferably, the (segmental) pre-image generated at the planning time (FIG. 2a) is matched with the CBCT-image (of the pre-alignment time) in order to determine the relative position between the actual arrangement 13 and the treatment body part 100. Preferably, the matching is performed by registering the pre-image with respect to the CBCT-image. The matching (in particular registration) is preferably performed under the condition that the treatment body part at the planning time is matched with the treatment body part at the pre-alignment time. The matching can be rigid or non-rigid. In particular the geometry (size and/or shape) of the treatment body part represented in the pre-image is matched (in particular registrated) with the geometry (size and/or shape) of the treatment part described by the CBCT-image.

Preferably, the matching (in particular registration) is performed such that the matching of the treatment body parts shown in the pre-image and the CBCT image is the only condition when matching (registering) the two images which is to be met or this condition is given higher weight than the matching of other parts of the anatomical structure like the bony structure. In this way positional shifts between the bony structure 110 and the treatment part 100 at the planning time (shown in FIG. 2a) and the bony structure 110 and the treatment body part 100 at the pre-alignment time can have no or only minor influence on the matching (in particular registration) process. As shown in FIGS. 2b and 2c, the relative position $d_{2tb}$ between the bony structure 110 and the treatment body part 100 differs from the relative position as shown in FIG. 2a at the alignment time but has no influence on the (correct) positioning of the treatment body part in step 2c).

Preferably, based on the determined position of the treatment body part 100 at the pre-alignment time (in step 2b) and based on the known position of the actual arrangement 13 in step 2b, the alignment control data are determined and output in order to control the position of the couch and/or the actual arrangement (relative to the treatment device 10). In particular, for this correction, only the position of the arrangement 13 is changed (if this is possible) with respect to the treatment device 10 since a movement of the couch 60 and thus of the patient 20 with respect to the treatment device 10 could have an influence on the relative position between the bony structure 110 and the treatment body part 100 (due to the influence of gravity). Of course, it is also within the gist of the present invention to control the position of the couch 60 and to thus change the position of the patient relative to the treatment device 10 based on the alignment control data.

FIG. 2c refers to the situation at the alignment time, i.e. the treatment body part has been aligned with the actual arrangement by means of the alignment control data. As shown in FIG. 2c, the alignment is correct, although the relative position $d_{2tb}$ between the treatment body part 100 and the bony structure 110 is different from the relative position $d_{1tb}$ shown in FIG. 2a. This is due to the property of the CBCT image which shows both the bony structure and the soft tissue structure of which the treatment body part is a part. In particular, the matching is a rigid matching, i.e. without deformation of the images under the aforementioned conditions. The aforementioned registration is in particular performed by transforming the different sets of image data (e.g. the pre-image and the CBCT-image) into a common reference system.

After the treatment body part has been aligned in accordance FIG. 2c, preferably the treatment is started by issuing the treatment beam from the beam source 12 which adopts positions in accordance with the actual arrangement 13 so that the treatment beam adopts the positions of the actual arrangement 13. After some time (which may be at regular intervals or which may depend on the treatment plan or on the radiation dose or on other conditions) the position of the patient is monitored by means of generating x-ray images. FIG. 2d shows a schematic example for the situation at the monitoring time. The x-ray images represent a bony structure and in particular do not or (for matching purposes) not clearly enough represent the treatment body part. The relative position between the x-ray imaging geometries and the reference system of the CBCT image is known. Thus, by generating the DRRs from the CBCT image, the position $d_{1ba}$ of the bony structure 110 relative to the actual arrangement 13 can be determined. Under the assumption that the relative position $d_{3tb}$ between the bony structure 110 and the treatment body part 100 at the monitoring time is the same as the relative position $d_{2tb}$ at the alignment time (step 2c), the position of the treatment body part 100 relative to the actual arrangement 13 can be determined. The relative position between the treatment body part 100 and the bony structure 110 is denoted as $d_{3tb}$. Thus, it is assumed that $d_{3tb}=d_{2tb}$. This assumption is generally more likely than assuming that $d_{2tb}=d_{1tb}$ since less time is elapsed between the situation shown in Figure c and the situation shown in Figure d and since the patient has not stood up or moved around between the alignment time and monitoring time but has only undergone small movements.

Based on the determined relative position $d_{4at}$ between the treatment body part 100 and the actual arrangement and based on a comparison of this relative position $d_{4at}$ with the planned relative position $d_{1at}$, preferably the x-ray based position control data are determined and outputted. The output control data cause in particular a change of position of the couch 60 and/or the actual arrangement 13 relative to the treatment body part. In particular, only the couch 60 is moved since it is to be assumed that the positional change is caused by a movement of the patient. Thus, a compensating movement of the couch 60 is likely to bring the anatomical structure which includes the bony structure 100 and the treatment body part 100 in the same relative position with respect to the gravity field as at the alignment time. This can increase the likelihood that the relative position between the bony structure 110 and the treatment body part 100 is the same as at the alignment time (after the correction has been performed in accordance with the x-ray based correction data). In summary, the x-ray based correction data (causing a movement of the couch and/or the actual arrangement) are likely to result in that $d_{4tb}$ is equal to $d_{3tb}$ and $d_{2tb}$, i.e. the relative positions are the same at the monitoring time and after the correction. That it is likely that the relative position $d_{5at}$ between the treatment body part 100 and the arrangement 13 is correct after the correction as shown in step 2e).

FIG. 2f refers to a later point in time which is after the correction. In particular, between the time of correcting shown in FIG. 2e and the time of another monitoring (e.g. second or, third monitoring etc.) there is a misalignment of the treatment body part 100 with respect to the actual arrangement 13. Again assuming that the relative position between the bony structure 110 and the treatment body part 100 (denoted as $d_{5tb}$) is the same as at the alignment time, i.e. $d_{5tb}=d_{2tb}$, then steps corresponding to the steps shown in FIGS. 2c, 2d, 2e, and 2f can be repeated. Thus, there is preferably a matching, in particular registration of the bony structure 110 of FIG. 2c with the bony structure 110 of FIG. 2f. This results in a determination of the position of the treatment body part 100 with respect to the actual arrangement 13 (under the aforementioned assumption) in a manner corresponding to step 2d. Based on this determination again x-ray based correction data are output which result in a correction of the position of the treatment body part 100 to be in line with the planning position in a manner corresponding to step 2e). Then again a third monitoring corresponding to step 2f) can be performed.

According to an embodiment, the delivery of treatment radiation is interrupted after determining that a correction of the position is required and is continued after correcting the position.

Figures 3, 3A, 3B:
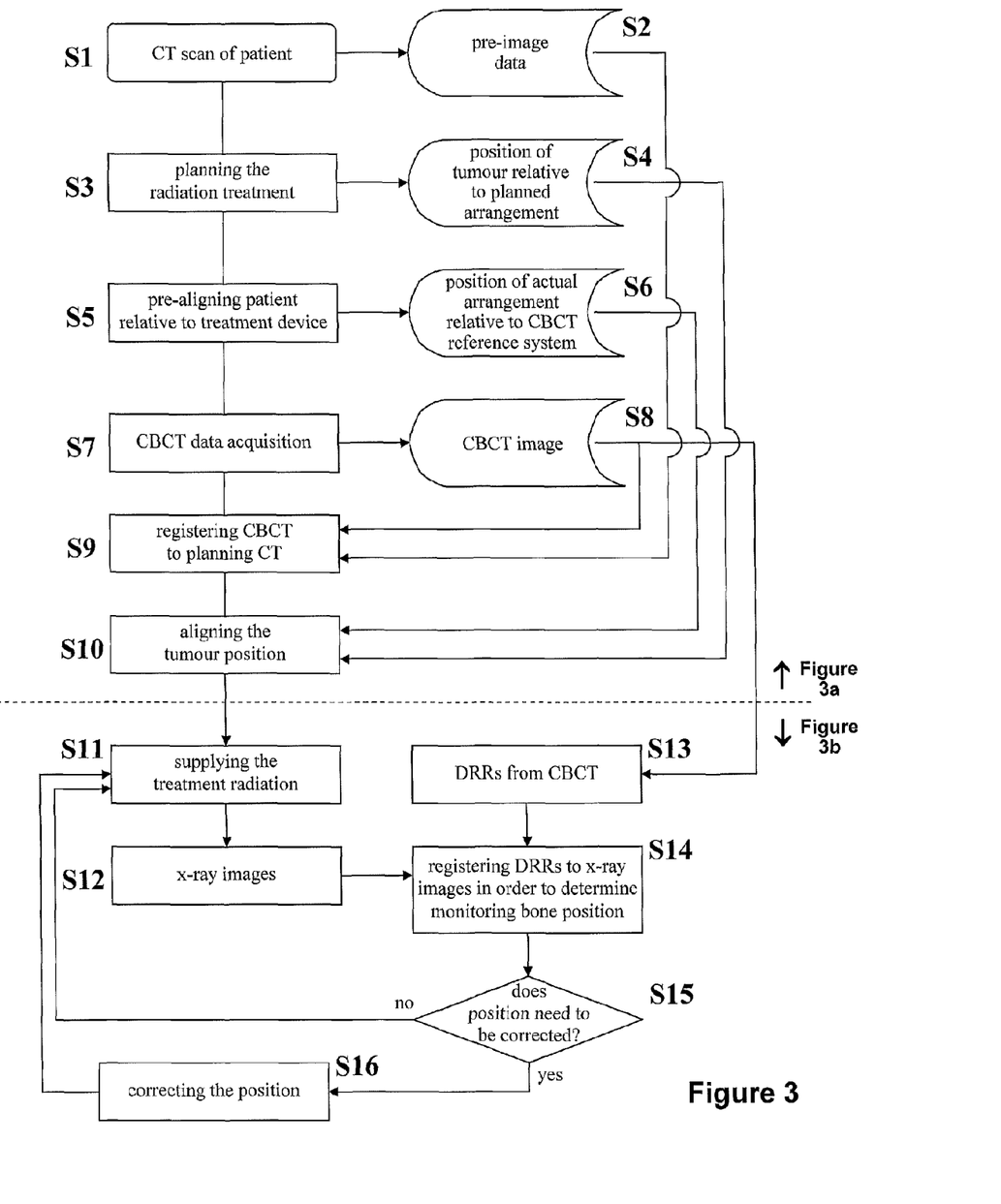
FIGS. 3a and 3b explain the steps of a method according to an embodiment of the invention.

FIG. 3 shows a flow diagram explaining a sequence of steps in accordance with an embodiment of the invention. FIG. 3a relates to the steps until the alignment time and FIG. 3b relates to the steps after the alignment time and in particular to the steps during treatment of the treatment body part by means of the treatment radiation.

According to a step S1, a CT scan of a patient is performed which results in pre-image data which are stored in step S2. According to step S3 a radiation treatment planning is performed which results in a planned relative position $d_{1at}$ of the treatment body part 100 (e.g. tumor) relative to a planned arrangement 13' of beam positions. The planned relative position $d_{1at}$ (see FIG. 2a) is stored in step S3.

Usually after some hours or on another day, a patient is pre-aligned with respect to the treatment device 10 (e.g. placed on the couch 60 of the treatment system according to step S4). The actual arrangement 13 is set by an operator which results in that there is a known relative position of the actual arrangement 13 relative to treatment device 10 and thus relative to the CBCT reference system (within which the CBCT image is resting). This position of the actual arrangement 13 relative to the CBCT reference system is known to the data processing method and in particular available in a data storage by accessing the data storage (step S5). Then in step S6 the CBCT data are acquired in order to generate a three-dimensional CBCT image in step S7. In step S8 the three-dimensional CBCT image is registered to the three-dimensional CT image. In step S9 an alignment of the position of the treatment body part (e.g. tumor) is performed based on the registration S8 and based on the data of steps S3 and S5. The alignment results in a change from $d_{2at}$ to $d_{3at}$ (see FIGS. 2b to 2c).

FIG. 3b refers to the x-ray based correction of the relative position between the actual arrangement and the anatomical structure. According to S10, the treatment is started and continued by delivering treatment radiation. After some time in step S11 x-ray images are generated (preferably stereoscopic x-ray images) for monitoring the position of the bony structure 110. In step S12 DRRs are generated from the three-dimensional CBCT image. In step S13 the DRRs are registered (FIG. 2d) to the x-ray images in order to determine a deviation of the monitoring tissue position ($d_{4at}$) from the planned relative position $d_{1at}$ in particular under the assumption that the relative position between the treatment body part 100 and the bony structure 110 has not changed from the pre-alignment time to the monitoring time. The registration of the DRRs to the x-ray images allows to determine the position of the part at the monitoring time relative to the actual arrangement.

In the step S14 it is checked whether a correction is required (for instance whether there is no deviation or a deviation above a predetermined threshold from the planned relative position). If no correction is required, the delivery of the treatment radiation is continued. If a correction is required, then the correction is performed in step S15 (which results in the corrected position $d_{5at}$ shown in FIG. 2e) and the delivery of radiation is continued after the correction by restarting the procedure at step S10. After some time of treatment, again x-ray images are generated according to step S11 which corresponds to the situation shown in FIG. 2f.

The present application is also directed to a further (second) independent invention which can be combined with the previously described invention. If the terms used in the following are identical with previously used terms, then they have the same meaning as in the above-described invention. The further invention is in particular directed to the following embodiments:

A. Data processing method for use in the field of radiation therapy and for determining a difference in position of a bony structure and/or whether there is this difference, wherein an anatomical structure of a patient includes the bony structure and a treatment body part to be treated by a treatment beam of a treatment device, the data processing method being constituted to be performed by a computer and comprising the following steps:

providing CBCT data describing a three dimensional CBCT image of a region which includes the anatomical structure, the CBCT image representing the bony structure at a time called pre-alignment time;

optionally providing target position data describing a target position which is a relative position between the bony structure and an actual arrangement of at least one position of the treatment beam;

providing CBCT position data describing the relative position between the CBCT image and the actual arrangement;

determining a position called bone CBCT position describing the relative position between the bony structure and the actual arrangement based on the CBCT data and the CBCT position data;

optionally, in case of a controlled change of position of the anatomical structure after generation of the CBCT image, providing position change data describing the change of position of the anatomical structure relative to the actual arrangement and determining a position called changed position which describes the relative position between the bony structure and the actual arrangement based on the bone CBCT position and the change of position and;

providing x-ray data describing information on a position of the bony structure, called monitoring bone position, relative to the actual arrangement at a point in time, called monitoring time, the monitoring time being after the pre-alignment time;

determining a difference or whether there is a difference optionally between the monitoring bone position and the target position and/or optionally between the monitoring bone position and the changed position, in case there was a controlled change and/or between the monitoring bone position and the bone CBCT position.

B. The data processing method of the above embodiment A, wherein x-ray data are repeatedly provided at subsequent points in time and a position of the bony structure relative to the actual arrangement is repeatedly determined based on the x-ray data, the position is called bony structure position and in particular the following is repeatedly performed:

determining a difference or whether there is a difference optionally between the most recently determined bony structure position and the target position and/or between the most recently determined bony structure position and a previously determined bony structure position which can also be the monitoring bone position and/or optionally between the bony structure position and the changed position, in case there was a controlled change and/or between the bone structure position and the bone CBCT position.

In particular, the method can comprise the optional step of compensating the determined difference only in case the difference between subsequent positions or difference between the previous position and the later position is above a predetermined threshold (called action threshold). According to a further embodiment, an indication signal (e.g. a visual, audio and/or tactile signal) is issued in accordance with a further step of the method in case the determined difference is above the predefined threshold in particular to warn the staff members that a reposition of the patient can be necessary in order to achieve good treatment result. In particular, the generation of a further CBCT image can be initiated in case the difference is above the predefined threshold, in order to determine if the relative position between the treatment body part and the bony structure has changed.

The above-described second invention in particular uses the bony structure shown in x-ray images as an indicator for the position of the treatment body part, in particular as an indicator whether the treatment body part is still in the correct position or has left the correct position. In particular, it is assumed that the treatment body part is in the correct position relative to the actual arrangement if the bony structure position coincides with the above-mentioned target position. In particular in addition to the CBCT image, x-ray images are generated for determining a change of the bony structure position which is used as an indicator. The CBCT data are preferably used for determining this change. Thus, preferably subsequent to the CBCT image, at least one x-ray image is generated. Preferably the at least one x-ray images are repeatedly generated at later points in time in order to track any movements of the bony structure during the treatment.

In particular the above step of providing the x-ray data includes:
  providing x-ray image data describing at least one two-dimensional x-ray image of the anatomical structure, the at least one two-dimensional x-ray image representing the bony structure (110) and the x-ray data being generated at a point in time (FIG. 2d); and
  providing x-ray geometry data describing a positional relationship between the actual arrangement (13) and at least one imaging geometry, called x-ray imaging geometry, given for generating the at least one x-ray image, and, at least in case of only one x-ray image, describing information on a size of the represented bony structure (110) in dependence on the position of the bony structure with respect to the imaging geometry.

According to a further embodiment of the further invention, the data processing method comprises the following:

The data processing (of the further invention) as described in one of the above embodiments and comprising the following step:
  determining data called therapy control data in dependence on the determined difference for controlling the relative position between the actual arrangement and the bony structure so that the determined difference is compensated.

The data processing method preferably further includes the step of outputting the therapy control data in order to control the relative position between the couch and the actual arrangement.

Preferably, the therapy control data are determined and/or output each time a new x-ray data has been generated based on which the position of the bony structure relative to the actual arrangement can be determined. To this end, preferably control data called x-ray imaging control data are generated which are constituted to cause the generation of the x-ray image data in particular after a period of time during which the treatment body part has been treated by the treatment beam.

The position of the bony structure can be determined in various manners based on the x-ray data and optionally based on the CBCT data and optionally also based on the CBCT position data. As described above with respect to the first invention, the three-dimensional CBCT image can be registered with respect to the at least one x-ray image. The positional change (for instance rotatorical and/or translatorical change) of the three-dimensional CBCT image in order to achieve the registration allows to determine a difference between the bone CBCT position and the monitoring bone position. Thus, based on the bone CBCT position and the determined difference, the monitoring bone position can be determined. This registration can be repeated for the different x-ray data generated repeatedly in order to repeatedly determine the bony structure position.

As mentioned with respect to the first invention, the registration can be performed based on image features by for instance generating DRRs from the CBCT image and matching those DRRs with the at least one x-ray image. According to a further embodiment, the registration can be based on features, in particular two- or three-dimensional models of the bony structure generated from the three-dimensional CBCT image. Thus, in particular the determination of the difference between the subsequent bony structure positions can be based on the image information included in the three-dimensional CBCT image or based on features of the bony structure extracted from the three-dimensional CBCT image. In particular, the above-described matching imaging geometry used with respect to the first invention can be used in order to determine the difference between the subsequent positions. Thus, the method in particular comprises the following steps:
  determining at least one two-dimensional digitally reconstructed radiograph (DRR) from the three-dimensional CBCT image which matches the at least one x-ray image, the matching at least one two-dimensional digitally reconstructed radiograph (DRR) resulting from a simulation of at least one imaging geometry given for generating the at least one two-dimensional digitally reconstructed radiograph (DRR), the imaging geometry being called matching imaging geometry, wherein the matching is performed based on the bony structure (110) shown in both the at least one two-dimensional digitally reconstructed radiograph (DRR) and the at least one x-ray image;
  providing a relative position between the at least one matching imaging geometry and the actual arrangement.

The monitoring bone position is an example for a bony structure position.

The further invention also encompasses the following embodiment:

Data processing method for use in the field of radiation therapy and for verifying the position ($d_{4at}$) of a treatment body part (100) relative to an actual arrangement (13) of at least one position of a treatment beam issued by a treatment device (10), the position ($d_{4at}$) being called monitoring tissue position and the treatment body part (100) being a soft tissue part of an anatomical structure of a patient; the data processing method being constituted to be performed by a computer (50) and comprising the following steps:
  providing (S6, S7) CBCT data describing a three-dimensional CBCT image of the volume encompassing the target region, the three dimensional CBCT image including the bony structure (110) at a point in time, called pre-alignment time (FIG. 2b);
  determining a rotational and/or translational registration offset that will bring the CBCT volume and the contained structures in the correct position relative to said actual arrangement;

applying said registration offset to either the patient or the actual arrangement to modify the relative position between the patient and the actual arrangement;

providing (S11) x-ray data describing information on a position ($d_{1ba}$) of the bony structure (110), called monitoring bone position ($d_{1ba}$), relative to the actual arrangement (13) at a point in time during treatment, called monitoring time (FIG. 3d), the monitoring time being after the pre-alignment time (FIG. 2b);

Comparing the position of the bony structures in the registered CBCT data with the position of the bony structures in the x-ray data to establish a position difference.

Comparing said position difference with an action threshold that determines the need to reposition the patient during the treatment.

The invention claimed is:

1. A data processing method in the field of radiation treatment for determining a monitoring tissue position of a treatment body part relative to an actual arrangement of at least one position of a treatment beam issued by a treatment device, the treatment body part being a soft tissue part of an anatomical structure of a patient, the data processing method being constituted to be performed by a computer and comprising:

providing cone-beam computed tomography (CBCT) data describing a three-dimensional CBCT image of the anatomical structure, the three dimensional CBCT image representing the treatment body part and a bony structure in a relative position to each other, called tissue-bone pre-alignment position, the CBCT image being generated at a point in time, called pre-alignment time, wherein the pre-alignment time is a time at which the patient is placed for alignment with respect to the treatment device and wherein the pre-alignment time is after a planning time at which a pre-image as a basis for planning a relative position between the treatment body part and a planned arrangement of the at least one position of the treatment beam of the treatment device is generated;

providing x-ray data describing information on a position of the bony structure, called monitoring bone position, relative to the actual arrangement at a point in time during treatment, called monitoring time, the monitoring time being after the pre-alignment time; and determining the monitoring tissue position of the treatment body part relative to the actual arrangement based on:
the tissue-bone pre-alignment position represented by the CBCT data;
the monitoring bone position described by the x-ray data; and
a tissue-bone monitoring position which describes a relative position between the treatment body part and the bony structure at the monitoring time, the tissue-bone monitoring position being set based on a predefined function of identity and the tissue-bone pre-alignment position, wherein according to the function of identity the treatment body part performs a positional change which is identical with the positional change of the bony structure.

2. The method of claim 1, wherein the step of providing the x-ray data includes:
providing x-ray image data describing at least one two-dimensional x-ray image of the anatomical structure, the at least one two-dimensional x-ray image representing the bony structure and the x-ray data being generated at the monitoring time; and
providing data describing a positional relationship between the actual arrangement and x-ray beams given for generating the at least one x-ray image, and, at least in case of only one x-ray image, describing information on a size of the represented bony structure in dependence on the position of the bony structure with respect to the x-ray beams.

3. The method of claim 2, wherein the step of determining the monitoring tissue position comprises:
determining at least one two-dimensional digitally reconstructed radiograph from the three-dimensional CBCT image which matches the at least one x-ray image, the matching at least one two-dimensional digitally reconstructed radiograph resulting from a simulation of at least one imaging geometry given for generating the at least one two-dimensional digitally reconstructed radiograph, the imaging geometry being called matching imaging geometry, wherein the matching is performed based on the bony structure shown in both the at least one two-dimensional digitally reconstructed radiograph and the at least one x-ray image;
providing a relative position between the at least one matching imaging geometry and the actual arrangement; and
determining the monitoring tissue position further based on:
the relative position between the at least one matching imaging geometry and the actual arrangement; and
the relative position between the at least one x-ray imaging geometry given when generating the matched at least one x-ray image and the actual arrangement.

4. The method of claim 1, wherein the step of determining the monitoring tissue position comprises:
determining the monitoring bone position based on the x-ray data, CBCT x-ray data and CBCT position data or only based on the x-ray data, the CBCT position data describing the relative position between the CBCT image and the actual arrangement, the CBCT x-ray data describe the relative position between the imaging geometry of the x-ray device and the position of the CBCT image, the imaging geometry being present when generating the at least one x-ray image; and
determining the monitoring tissue position based on the determined monitoring bone position and the set predefined relationship.

5. The method of claim 1, further comprising:
providing planning data describing a planned relative position between the treatment body part and a planned arrangement of at least one position of a treatment beam to be issued by the treatment device.

6. The method of claim 5, further comprising:
providing data, called CBCT arrangement data describing the relative position between the anatomical structure described by tine the three-dimensional CBCT image and the actual arrangement at the pre-alignment time, the relative position being called pre-alignment CBCT position;
providing data, called separation data, describing a position of the treatment body part within the anatomical structure, the position being called tissue structure position;
determining a position of the treatment body part relative to the actual arrangement at the pre-alignment time, called pre-alignment tissue position, based on the pre-alignment CBCT position and the tissue structure position;

determining a difference in positions, called pre-alignment difference, between the planned relative position and the pre-alignment tissue position; and determining control data, called alignment control data, in dependence on the pre-alignment difference, for controlling a relative position between the treatment both part and the actual arrangement to correspond to the planned relative position and outputting the alignment control data before the monitoring time.

7. The method of claim 6, wherein the predefined relationship describes that the tissue-bone pre-alignment position is identical with the tissue-bone monitoring position or the predefined relationship describes a deviation from the identity in dependence on the pre-alignment difference.

8. The method of claim 6, wherein the planning data comprises a description of a three-dimensional image of the anatomical structure which is called pre-image and with respect to which the planned relative position is defined and wherein the step of determining the pre-alignment difference comprises matching the pre-image and the CBCT image based on the treatment body part represented in the pre-image and the CBCT image.

9. The method of claim 6, further comprising determining control data, called x-ray based control data, the determining the control data comprising:

determining a difference, called correction difference, between the determined monitoring tissue position and the provided planned relative position;

determining control data, called x-ray based position control data, in dependence on the correction difference, for controlling the relative position between the actual arrangement and the treatment body part to correspond to the planned relative position; and outputting the x-ray based position control data.

10. The method of claim 1, further comprising:

generating control data, called x-ray imaging control data, for causing generation of the x-ray image data after a period of time during which the treatment body part has been treated by the treatment beam.

11. The method of claim 10, wherein the steps of outputting the x-ray imaging control data, receiving the x-ray image data, determining the x-ray based position control data based on the lastly provided x-ray data and outputting the x-ray based position control data are repeated during treatment of the treatment body part for controlling a position of the treatment both part to be in line with the planned relative position.

12. A non-transitory computer program storage medium comprising a program which, when running on an associated computer or when loaded onto the computer, causes the computer to perform a method in the field of radiation treatment for determining a monitoring tissue position of a treatment body part relative to an actual arrangement of at least one position of a treatment beam issued by a treatment device, the treatment body part being a soft tissue part of an anatomical structure of a patient, the method comprising:

providing cone-beam computed tomography (CBCT) data describing a three-dimensional CBCT image of the anatomical structure, the three dimensional CBCT image representing the treatment body part and a bony structure in a relative position to each other, called tissue-bone pre-alignment position, the CBCT image being generated at a point in time, called pre-alignment time, wherein the pre-alignment time is a time at which the patient is placed for alignment with respect to the treatment device and wherein the pre-alignment time is after a planning time at which a pre-image as a basis for planning a relative position between the treatment body part and a planned arrangement of the at least one position of the treatment beam of the treatment device is generated;

providing x-ray data describing information on a position of the bony structure, called monitoring bone position, relative to the actual arrangement at a point in time during treatment, called monitoring time, the monitoring time being after the pre-alignment time; and determining the monitoring tissue position of the treatment body part relative to the actual arrangement based on:

the tissue-bone pre-alignment position represented by the CBCT data;

the monitoring bone position described by the x-ray data; and a tissue-bone monitoring position which describes a relative position between the treatment body part and the bony structure at the monitoring time, the tissue-bone monitoring position being set based on a predefined function of identity and based on the tissue-bone pre-alignment position, wherein according to the function of identity the treatment body part preforms a positional change which is identical with the positional change of the bony structure.

13. A computer which comprises the non-transitory computer storage medium of claim 12.

14. A radiotherapy system, comprising:

the computer of claim 13;

the treatment device for treating the treatment body part with the actual arrangement;

a couch for placing the patient, the treatment device constituted for treating the treatment body part, if the patient is placed on the couch for treatment;

a CBCT-device constituted for generating the three-dimensional CBCT image and for generating the at least one x-ray image, if the patient is placed on the couch for treatment and for outputting the three-dimensional CBCT image and the at least one x-ray image to the computer; or a CBCT-device constituted for generating the three-dimensional CBCT image and for outputting the three-dimensional CBCT image to the computer, and an x-ray device for generating the at least one x-ray image, if the patient is placed on the couch for treatment, and for outputting the at least one x-ray image to the computer.

15. The radiotherapy system of claim 14, wherein the system is configured so that the position of the couch relative to the position of the arrangement is controllable by the computer.

16. A method for controlling the radiotherapy system of claim 15, comprising issuing control signals from the computer to the couch and/or to the treatment device for changing the relative position between the couch and the arrangement.

* * * * *